United States Patent [19]

Vigante et al.

[11] 4,326,064
[45] * Apr. 20, 1982

[54] DERIVATIVES OF 1,4-DIHYDROPYRIDINE-3-CARBOTHIOL ACIDS

[76] Inventors: Brigita A. Vigante, ulitsa Dzirnavu, 46, kv. 6; Yan-Voldemar Y. Ozol, ulitsa Struktoru, 11, kv. 4; Rasma O. Vitolin, ulitsa Lielvardes, 26, kv. 39, all of Riga; Gunta O. Silenietse, ulitsa Mierv, 16/7, kv. 328, Rizhsky raion, Salaspils; Agris A. Kimenis, ulitsa Staitseles, 15, kv. 208; Gunar Y. Dubur, ulitsa Ierikju, 43, kv. 2, both of Riga, all of U.S.S.R.

[*] Notice: The portion of the term of this patent subsequent to Feb. 24, 1998, has been disclaimed.

[21] Appl. No.: 201,599

[22] Filed: Oct. 28, 1980

Related U.S. Application Data

[63] Continuation of Ser. No. 21,486, Mar. 19, 1979, Pat. No. 4,252,956.

[51] Int. Cl.³ .......................................... C07D 213/55
[52] U.S. Cl. ................................... 546/322; 546/263; 546/318; 424/266
[58] Field of Search ........................ 546/318, 322, 263

[56] References Cited

U.S. PATENT DOCUMENTS 3,923,818 12/1975 Bossert et al. ...................... 546/321
3,996,234 12/1976 Bossert et al. ...................... 546/321
4,252,956 2/1981 Vigante et al. ...................... 546/322

*Primary Examiner*—Alan L. Rotman
*Attorney, Agent, or Firm*—Lilling & Greenspan

[57] ABSTRACT

The present invention relates to compounds which are derivatives of 1,4-dihydropyridine-3-carbothiol acids of the formula:

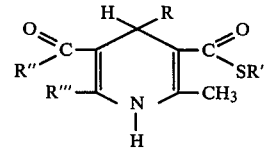

wherein
R is hydrogen, an alkyl, aryl, heteryl;
R' is a lower alkyl, aralkyl;
R" is an alkoxy, alkylthio, aralkylthio;
R''' is methyl;
R'''+R" is phenylene (ortho-).

The compounds of the present invention reveal a coronarodilating activity, and are useful in medicine.

2 Claims, No Drawings

DERIVATIVES OF 1,4-DIHYDROPYRIDINE-3-CARBOTHIOL ACIDS

This is a continuation, of application Ser. No. 21,486, filed Mar. 19, 1979 now U.S. Pat. No. 4,252,956 issued Feb. 4, 1981.

FIELD OF THE INVENTION

The present invention relates to biologically active chemical compounds and, more specifically, it relates to derivatives of 1,4-dihydropyridine-3-carbothiol acids.

The compounds according to the present invention reveal a coronarodilating activity, and are useful in medicine.

BACKGROUND OF THE INVENTION

Known in the art are derivatives of 1,4-dihydropyridines such as 2-methyl-3-alkoxycarbonyl-4-aryl-5-oxo-1,4-dihydroindeno-(1,2-b)-pyridines. However, their biological activity is not described in the literature. Also known are derivatives of 1,4-dihydropyridines such as 2,6-dimethyl-3,5-dicarbomethoxy-4-o-nitrophenyl-1,4-dihydropyridine which have a pronounced coronarodilating activity but are unstable in storage when exposed to light for long periods, they are also relatively toxic and possess insufficient selective effect (reduce the arterial pressure).

SUMMARY OF THE INVENTION

It is an object of the present invention to provide derivatives of 1,4-dihydropyridines having coronarodilating activity, low toxicity, and a high selectivity of the effect.

This object is accomplished by the provision of derivatives of 1,4-dihydropyridine-3-carbothiol acids of the general formula:

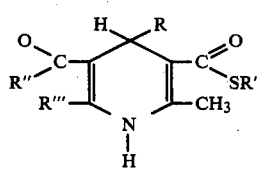

(I)

wherein
R is hydrogen, alkyl, aryl, heteryl;
R' is lower alkyl, aralkyl;
R" is alkoxy, alkylthio, aralkylthio;
R''' is methyl; R'''+R" is phenylene (ortho-).

The most interesting are the following compounds:
di-S-ethyl ester of 2,6-dimethyl-4-m-pyridyl-1,4-dihydropyridine-3,5-dicarbothiol acid having the formula:

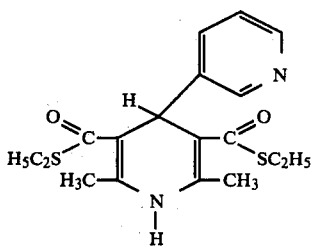

(II)

3-S-benzyl-5-ethyl ester of 2,6-dimethyl-4-phenyl-1,4-dihydropyridine-3-carbothiol-5-carboxylic acid having the formula:

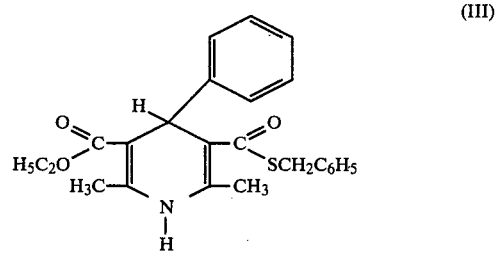

(III)

2-methyl-3-benzylthiocarbonyl-4-phenyl-5-oxo-1,4-dihydroindeno-(1,2-b)-pyridine having the formula:

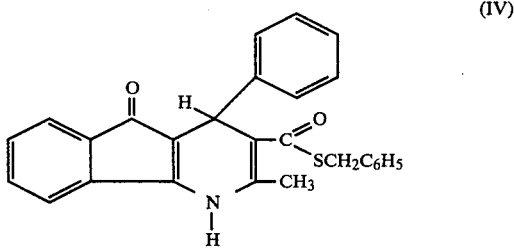

(IV)

2-methyl-3-benzylthiocarbonyl-4-o-hydroxyphenyl-5-oxo-1,4-dihydroindeno-(1,2-b)-pyridine having the formula:

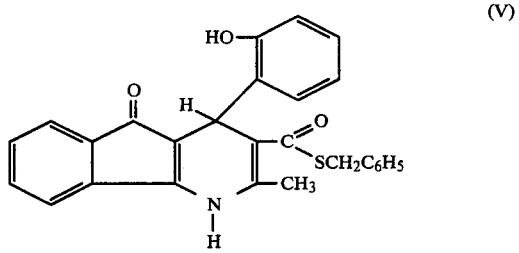

(V)

The compounds according to the present invention and the properties thereof have not been hitherto described in the literature.

The compounds of this invention comprise yellow to red crystalline compounds stable in storage in the air for a period as long as six months; these compounds are weak acids insoluble in water, sparingly soluble in ethanol, methanol, and acetic acid.

DETAILED DESCRIPTION OF THE INVENTION

Preparation of the compounds according to the present invention, wherein R is hydrogen, an alkyl, an aryl, a heteryl; R' is a lower alkyl, an aralkyl; R" is an alkylthio, an aralkythio; R''' is methyl, is effected by condensation of S-substituted esters of thioacetoacetic acid with aldehydes and ammonia in an alcohol upon heating.

The above-specified compounds, wherein R is $C_6H_4NO_2$ Para), R' is $C_2H_5$; R" is $SC_2H_5$; R''' is $CH_3$ are prepared by condensation of S-ethyl ester of β-aminothiocrotonic acid with p-nitrobenzylidene-S-ethyl ester of thioacetoacetic acid.

The compound, wherein R is $C_6N_4NO_2$ (para), R' is $C_2H_5$, R" is $C_2H_5$, R''' is $CH_3$ is prepared from an ethyl ester of β-aminocrotonic acid and a p-nitrobenzylidene-S-ethyl ester of thioacetoacetic acid.

Condensation of S-substituted esters of β-aminocrotonic acid with α-alkylidene and α-arylidene derivatives of ethyl ester of acetoacetic acid results in the preparation of asymmetric esters of 1,4-dihydropyridine series of the above-given general formula, wherein R is an alkyl, aryl; R' is a lower alkyl, an aralkyl; R" is $OC_2H_5$; and R''' is methyl.

Preparation of polycyclic derivatives of 1,4-dihydropyridines of the above-given general formula, wherein R is an aryl, R' is a lower alkyl, an aralkyl; R"+R''' is phenylene (ortho-) is effected by condensation of 2-arylidenindane-1,3-diones with S-substituted esters of β aminothiocrotonic acid in the medium of acetic acid upon short heating. The same derivatives with R=H are prepared by condensation of indan-1,3-dione, an aliphatic aldehyde and an S-substituted ester of β-aminothiocrotonic acid in a medium of toluene upon heating.

The compounds according to the present invention have been subjected to pharmacological investigations. In these investigations generally known methods were employed making it possible to obtain the effect of said compounds on the blood circulation system and vegetative nervous system. Tests of the compounds according to the present invention were performed in comparison with the prior art coronarodilating agents; carbocromene and ditrimine and with the prior art spasmolytic preparation—papaverine having a myotropic effect.

In experiments on narcotized cats recording the volume rate of coronary blood flow, it has been found that the compounds, according to the present invention, demonstrate a clearly pronounced coronarodilating activity, increasing the volume rate of the coronary blood flow as well as preventing the toxic effect of pituitrin on the heart. These compounds reveal their effect in a dose of 0.1 mg/kg when administered intravenously. The effect duration is 60 to 150 minutes. The most active are compounds II, III, VI and VII (see the Table hereinbelow). These compounds; activity are not inferior to prior art compounds such as ditrimine and carbocromene. Furthermore, the compounds according to the present invention are several times less toxic which is an advantage over the prior art preparations.

As to the duration of their effect the compounds according to the present invention are superior over papaverine by about 10 times. The coronarodilating effect is also observed when the compounds of this invention are administered perorally.

When administered intravenously, the compounds according to the present invention reveal a certain hypotensive effect which is substantially weaker than that of papaverine. When administered intragastrically, no noticeable change in heart activity or arterial pressure was observed.

The compounds according to the present invention exert influence upon functions of the vegetative nervous system. Thus, in doses of 0.005 to 3 mg/kg these compounds provide an adrenoblocking effect and, to a certain extent, a ganglioblocking effect, the depressive effect of acetylcholine being simultaneously decreased. The compounds according to the present invention also inhibit hemodynamic effects of serotonin.

In doses increasing the coronary blood flow, the compounds according to the present invention reveal antagonism to biogenic amines: adrenaline, acetylcholine and serotonin.

Acute toxicity of the compounds according to the present invention has been investigated in tests of white mice upon intraperitoneal administration. The results obtained in these experiments are given in the Table hereinbelow.

These compounds are considerably less toxic than papaverine, ditrimine, carbocromene.

Taking into consideration the coronarodilating activity of the compounds according to the present invention, their exclusively low toxicity and weak hypotensive activity, it can be expected that the compounds of this invention will be useful in medical practice as remedies for relaxation of spasms of coronary vessels.

TABLE

Comparative effect of derivatives of 1,4-dihydropyridine-3-carbothiol acids and the prior art preparations on the cardiovascular system

| Compound No. 1 | Dose increasing coronary blood flow by 30–50%, mg/kg 2 | Duration of the effect, min 3 | $ED_{30}$ of the hypotensive effect, mg/kg 4 | $LD_{50}$ for white mice upon intraperitoneal administration, mg/kg 5 |
|---|---|---|---|---|
| I | 1 | 60–90 | 1.8 | above 4,000 |
| II | 0.5 | above 120 | 0.56 | above 7.000 |
| III | 0.5 | 150 | 1.65 | above 6.000 |
| IV | 2–4 | 30–60 | 3.45 | above 6.000 |
| V | 3.0 | | 3.0 | above 2.000 |
| VI | 0.3 | | 1.0 | 2.000 |
| VII | 0.5 | | 1.0 | 2.000 |
| VIII | 3.0 | | 5.0 | above 2.000 |
| IX | 3.0 | | 1.0 | above 2.000 |
| X | 3.0 | | — | above 2,000 |
| Ditrimine | 0.5 | | 1.0 | 180 (149–218) |
| Carbocromene | 0.5 | | — | 640 (478–758) |
| Papaverine | 1 | 10–20 | 0.27 (0.05–0.49) | 91 (82.4–100.6) |

I Di-S-ethyl ester of 2,5-dimethyl-1,4-dihydropyridine-3,5-dicarbothiol acid
II D-S-ethyl ester of 2,6-dimethyl-4-m-pyridyl-1,4-dihydropyridine-3,5-dithiocarbathiol acid
III 3-S-Benzyl-5-ethyl ester of 4-phenyl-2,6-dimethyl-1,4-dihydropyridine-3-carbothiol-5-carboxylic acid
IV 3-S-Benzyl-5-ethyl ester of 2,4,6-trimethyl-1,4-dihydropyridine-3-carbothiol-5-carboxylic acid
V 2-Methyl-3-ethylthiocarbonyl-4-phenyl-5-oxo-1,4-dihydroindeno-(1,2-b)pyridine
VI 2-methyl-3-benzylthiocarbonyl-4-phenyl-5-oxo-1,4-dihydroindeno-(1,2-b)-pyridine
VII 2-Methyl-3-benzylthiocarbonyl-4-o-hydroxyphenyl-5-oxo-1,4-dihydroindeno-(1,2-b)-pyridine
VIII 2-Methyl-3-ethylthiocarbonyl-4-o-hydroxyphenyl-5-oxo-1,4-dihydroindeno (1,2-b)-pyridine
IX 2-Methyl-3-ethylthiocarbonyl-4-p-nitrophenyl-5-oxo-1,4-dihydroindeno-(1,2-b)-pyridine
X 2-Methyl-3-ethylthiocarbonyl-4-o-nitrophenyl-5-oxo-1,4-dihydroindeno(1,2-b)-pyridine For a better understanding of the present invention some specific Examples illustrating preparation of derivatives of 1,4-dihydropyridine-3-carbothiol acids are given hereinbelow.

EXAMPLE 1

Di-S-ethyl ester of 2,6-dimethyl-1,4-dihydropyridine-3,5-dicarbothiol acid

A mixture of 2.92 g (0.02 mole) of S-ethyl ester of thioacetoacetic acid, 1.38 g (0.06 mole) of urotropin and 0.7 g of ammonium acetate are heated at reflux for 5 min in 5 ml of methanol. The reaction mixture is allowed to stay for 12 hours at the temperature of 0° C.; a yellow precipitate is separated and crystallized from methanol. The yield is 2.1 g (74%), melting point is 142°–143° C.

Found, %: C 54.26; H 6.86; N 5.04; S 22.36.
C$_{13}$H$_{19}$NO$_2$S$_2$. Calculated, %: C 54.70; H 6.71; N 4.91; S 22.47.

UV-spectrum, $\lambda_{max}$=205, 278, 418 nm.

EXAMPLE 2

Di-S-benzyl ester of 2,6-dimethyl-1,4-dihydropyridine-3,5-dicarbothiol acid

The synthesis is carried out following the procedure of the foregoing Example 1, except that as the starting component use is made of an S-benzyl ester of thioacetoacetic acid.

The yield is 70%, melting point is 109°–110° C.

Found, %: C 67.26; H 5.54; N 4.09; S 14.97. C$_{23}$H$_{23}$NO$_2$S$_2$. Calculated, %: C 67.45; H 5.66; N 3.42; S 15.66.

UV-spectrum, $\lambda_{max}$=208, 278, 422 nm.

EXAMPLE 3

Di-S-ethyl ester of 2,4,6-trimethyl-1,4-dihydropyridine-3,5-dicarbothiol acid A mixture of 2.92 g (0.02 mole) of S-ethyl ester of thioacetoacetic acid and 0.92 g (0.015 mole) of ammonium aldehyde is heated to reflux for one hour in 10 ml of ethanol. Water is drained, the precipitate in the form of a yellow oil is recovered with ether and dried with anhydrous sodium sulphate. The oil remaining after separation of ether is purified by chromatography on a column packed with alumina (the eluent -chloroform-hexane-acetone taken in the ratio of 9:7:1 respectively). The solvent is removed and the precipitate is crystallized from a mixture of ethanol and hexane. The yield is 0.92 g (10%), melting point 116° C.

Found, %: C 56.26; H 7.16; N 4.65; S 20.95. C$_{14}$H$_{21}$NO$_2$S$_2$. Calculated, %: C 56.15; H 7.07; N 4.68; S 21.41.

UV-spectrum, $\lambda_{max}$=205, 255 (sh.), 277, 390 nm.

EXAMPLE 4

Di-S-ethyl ester of 2,6-dimethyl-4-phenyl-1,4-dihydropyridine-3,5-dicarbothiol acid A mixture of 4.38 g (0.03 mole) of S-ethyl ester of thioacetoacetic acid, 1.52 g (0.015 mole) of benzaldehyde and 1.5 ml of a 25% ammonium hydroxide is heated at reflux for 6 hours in 5 ml of ethanol. The product is poured into water, the precipitated yellow oil is purified by chromatography as in the foregoing Example 3. The yield is 0.9 g (15%), melting point is 132°–133° C.

Found, %: C 63.64; H 6.78; N 4.05; S 16.90. C$_{19}$H$_{23}$NO$_2$S$_2$. Calculated, %: C 63.12; H 6.41; N 3.87; S 17.75.

EXAMPLE 5

Di-S-ethyl ester of 2,6-dimethyl-4-m-pyridyl-1,4-dihydropyridine-3,5-dicarbothiol acid A mixture of 4.38 g (0.03 mole) of S-ethyl ester of thioacetoacetic acid, 1.6 g (0.015 mole) of m-pyridinaldehyde and 1.5 ml of a 25% ammonium hydroxide is heated at reflux for six hours in 5 ml of ethanol. The yellow precipitate formed upon cooling is crystallized from ethanol to give 2.18 g (40%) of the product melting at 241° C.

Found, %: C 59.06; H 6.04; N 7.74; S 17.21. C$_{18}$H$_{22}$N$_2$O$_2$S$_2$. Calculated, %: C 59.64; H 6.12; N 7.73; S 17.69.

UV-spectrum, $\lambda_{max}$=205, 255, 380 nm.

EXAMPLE 6

Diethyl ester of 2,4,6-trimethyl-1,4-dihydropyridine-3-carbothiol-5-carboxylic acid 2.98 g (0.02 mole) of S-ethyl ester of β-aminothiocrotonic acid and 3.12 g (0.012 mole) of α-ethylidenacetoacetic ether are heated at reflux for one hour in 5 ml of ethanol. After cooling for 12 hours at a temperature of 0° C. a yellowish compound is precipitated which is crystallized from a mixture of methanol and hexane. The yield is 3.9 g (69%), melting point is 110°–111° C.

Found, %: C 59.78; H 7.62; N 5.27; S 10.82. C$_{14}$H$_{21}$NO$_3$S. Calculated, %: C 59.34; H 7.47; N 4.84; S 11.31.

UV-spectrum, $\lambda_{max}$=203, 252 (sh.), 273, 382 nm.

EXAMPLE 7

3-S-benzyl-5-ethyl ester of 2,4,6-trimethyl-1,4-dihydropyridine-3-carbothiol-5-carboxylic acid The condensation process is effected in a manner similar to that of Example 6 hereinabove. From 4.12 g (0.02 mole) of S-benzyl ester of β-aminothiocrotonic acid and 3.12 g (0.02 mole) of α-ethylidenacetoacetic ether there are obtained 3.8 g (55%) of a yellow product melting at 153° C.

Found, %: C 66.19; H 6.31; N 4.29; S 8.54. C$_{19}$H$_{23}$NO$_3$S. Calculated, %: C 66.05; H 6.71; N 4.05; S 9.28.

UV-spectrum, $\lambda_{max}$=203, 250 (sh.), 270, 378 nm.

EXAMPLE 8

3-S-benzyl-5-ethyl ester of 4-phenyl-2,6-dimethyl-1,4-dihydropyridine-3-carbothiol-5-carboxylic acid The condensation is carried out following the procedure of Example 6 hereinbefore. From 4.12 g (0.02 mole) of S-benzyl ester of β-aminothiocrotonic acid and 4.38 g (0.02 mole) of α-benzylidenacetoacetic ether upon heating for 6 hours in 5 ml of ethanol there are obtained 3.1 g (38%) of a yellowish compound melting at 159° C.

Found, %: C 69.98; H 6.07; N 3.74; S 6.98; C$_{24}$H$_{25}$NO$_3$S. Calculated, %: C 70.73; H 6.18; N 3.44; S 7.87.

UV-spectrum, $\lambda_{max}$=203, 258, 380 nm.

EXAMPLE 9

Diethyl ester of 4-phenyl-2,6-dimethyl-1,4-dihydropyridine-3-carbothiol-5-carboxylic acid 1.49 g (0.01 mole) of S-ethyl ester of β-aminothiocrotonic acid and 2.19 g (0.01 mole) of α-benzylidenacetoacetic ether are heated for six hours in 5 ml of ethanol to give 1.9 g (55%) of a yellow substance melting at 152°–154° C. (from methanol).

Found, %: C 65.69; H 6.63; N 4.35; S 9.56; C$_{19}$H$_{23}$C$_3$NS. Calculated, %: C 66.03; H 6.71; N 4.06; S 9.28.

UV-spectrum, $\lambda_{max}$=205, 260, 380 nm.

EXAMPLE 10

2-methyl-3-benzylthiocarbonyl-4-phenyl-5-oxo-1,4-dihydroindeno-(1,2-b)-pyridine A mixture of 1.17 g (0.005 mole) of 2-benzylidene-1,3-indandione and 1.04 g (0.005 mole) of S-benzyl ester of β-amino thiocrotonic acid is heated at reflux in 5 ml of glacial acetic acid for 5 minutes. After cooling a dark-red compound is isolated in yield of 1.23 g (58%) melting at 226°–228° C. (from acetic acid).

Found, %: C 76.68; H 4.97; N 3.29; S 8.01; $C_{27}H_{21}NO_2S$. Calculated, %: C 76.57; H 5.00; N 3.31; S 7.57.

UV-spectrum, $\lambda_{max}$=203, 238 (sh.), 268, 355, 495 nm.
IR-spectrum, cm$^{-1}$; $\nu_{C=O}$=1,645; 1,650; $\nu_{N-H}$=3,300.

EXAMPLE 11

2-methyl-3-ethylthiocarbonyl-4-phenyl-5-oxo-1,4-dihydroindeno-(1,2-b)-pyridine The synthesis is carried out in a manner similar to that described in Example 10 hereinabove, except that as the starting compound use is made of S-ethyl ester of β-aminothiocrotonic acid. The yield is 87%, melting point is 248°–249° C.

Found, %: C 73,00; H 5.61; N 4.01; S 9.00. $C_{22}H_{19}NO_2S$. Calculated, %: C 73.10; H 5.30; N 3.88; S 8.87.

UV-spectrum, $\lambda_{max}$=203, 238, 268, 355, 495 nm.
IR-spectrum, cm$^{-1}$: $\nu_{C=O}$=1,655; 1,680; $\nu_{N-H}$=3,620.

EXAMPLE 12

2-methyl-3-benzylthiocarbonyl-4-o-hydroxyphenyl-5-oxo-1,4-dihydroindeno-(1,2-b)-pyridine The synthesis is carried out in a manner similar to that described in Example 10 hereinabove, except that as the starting component use is made of o-hydroxybenzylideno-1,3-indandione.

The yield is 78%; melting point of the product is 247° C.

Found, %: C 73.48; H 4.84; N 3.30; S 7.25. $C_{27}H_{21}NO_3S$. Calculated, %: C 73.78; H 4.82; N 3.19; S 7.30.

UV-spectrum, $\lambda_{max}$=203, 220 (sh.), 262, 305 (sh.), 460 nm.

IR-spectrum, cm$^{-1}$: $\nu_{C=O}$=1,655; 1,680; $\nu_{N-H}$=3,210.

EXAMPLE 13

2-methyl-3-ethylthiocarbonyl-4-o-hydroxyphenyl-5-oxo-1,4-dihydroindeno-(1,2-b)pyridine The synthesis is conducted following the procedure of Example 10 hereinbefore, except that as the starting components use is made of S-ethyl ester of β-aminothiocrotonic acid and o-hydroxybenzylidenindan-1,3-dione. The yield is 79%; the product melting point is 225°–227° C.

Found, %: C 69,92; H 4.90; N 3.95; S 8.23. $C_{22}H_{19}NO_3S$. Calculated, %: C 70.00; H 5.07; N 3.71; S 8.50.

UV-spectrum, $\lambda_{max}$=203, 220 (sh.), 263, 460 nm.
IR-spectrum, cm$^{-1}$: $\nu_{C=O}$=1,660; 1,690; $\nu_{N-H}$=3,220.

EXAMPLE 14

2-methyl-3-ethyl-thiocarbonyl-4-p-nitrophenyl-5-oxo-1,4-dihydroindeno-(1,2-b)-pyridine The synthesis is conducted as in Example 10, except that as the starting components use is made of S-ethyl ester of β-aminoethiocrotonic acid and p-nitrobenzylidenindane-1,3-dione. The product yield is 74%, melting point 238° C.

Found, %: C 65.20; H 4.59; N 6.54; S 7.65. $C_{22}H_{18}N_2C_4S$. Calculated, %: C 65.01; H 4.46; N 6.89; S 7.89.

UV-spectrum, $\lambda_{max}$=203, 263; 295 (sh.), 340, 495 nm.
IR-spectrum, cm$^{-1}$: $\nu_{C=O}$=1,630; 1,645; $\nu_{N-H}$=3,280.

EXAMPLE 15

2-methyl-3-ethylthiocarbonyl-4-o-nitrophenyl-5-oxo-1,4-dihydroindeno-(1,2-b)-pyridine The synthesis is conducted as in Example 10, except that as the starting components use is made of S-ethyl ester of β-aminothiocrotonic acid and o-nitrobenzylidenindane-1,3-dione. The product yield is 82%, melting point 221° C.

Found, %: 64.50; H 4.47; N 6.50; S 7.28. $C_{22}H_{18}N_2O_4S$. Calculated, %: C 65.01; H 4.46; N 6.89; S 7.89.

UV-spectrum, $\lambda_{max}$=203, 266, 345, 495 nm.
IR-spectrum, cm$^{-1}$: $\nu_{C=O}$=1,655; 1,680; $\nu_{N-H}$=3,320.

EXAMPLE 16

2-methyl-3-ethylthiocarbonyl-5-oxo-1,4-dihydroindeno-(1,2-b)-pyridine 2.98 g (0.02 mole) of S-ethyl ester of β-aminothiocrotonic acid, 2.92 g (0.02 mole) of indane-1,3-dione and 0.7 g of paraform are heated at reflux in 30 ml of toluene for 20 minutes under vigorous stirring in a flask provided with Dean-Starkpacking. There is distilled-off about 10 ml of the solvent; after cooling to a temperature of 0° C. 1.42 g (25%) a red substance is isolated which melts at 240° C. (from acetic acid).

Found, %: C 66.98 H 5.01; N 4.59; S 10.87. $C_{16}H_{15}NO_2S$. Calculated, %: C 67.32; H 5.26; N 4.91; S 11.23.

UV-spectrum, $\lambda_{max}$=203, 232, 266, 304, 320 (sh.), 348, 502 nm. IR-spectrum, cm$^{-1}$: $\nu_{C=O}$=1,630; 1,660; $\nu_{N-H}$=3,230.

EXAMPLE 17

2,4-dimethyl-3-ethylthiocarbonyl-5-oxo-1,4-dihydroindeno-(1,2-b)-pyridine

In a manner similar to that described in the foregoing Example 16, from 2.98 g (0.02 mole) of S-ethyl ester of β-aminothiocrotonic acid, 2.92 g (0.02 mole) of indane-1,3-dione and about a 10-times excess of acetaldehyde there is obtained 1.2 g (20%) of a red-brown substance melting at 189°–190° C. (from acetic acid).

Found, %: C 73.92; H 5.41; N 4.58; S 10.96. $C_{17}H_{17}NO_2S$. Calculated, %: C 74.22; H 5.68; N 4.67; S 10.67.

UV-spectrum, $\lambda_{max}$=203, 234, 266, 301, 319 (sh.), 345, 485 nm.
IR-spectrum, cm$^{-1}$: $\nu_{CO}$=1,640; 1,660; $\nu_{N-H}$=3,280.

What is claimed is:

1. A compound of 1,4-dihydropyridine-3-carbothiol acid having the following structure:
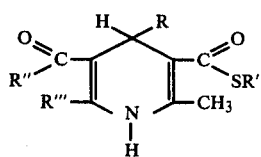
wherein
R is hydrogen, lower alkyl, phenyl, or pyridyl;
R' is lower alkyl, or benzyl;
R" is lower alkoxy;
R''' is methyl.
2. 3-S-benzyl-5-ethyl ester of 2,6-dimethyl-4-phenyl-1,4-dihydropyridine-3-carbothiol-5-carboxylic acid having the following formula:
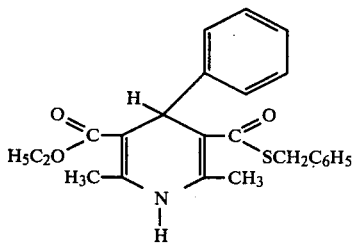
* * * * *